(12) United States Patent
Chen et al.

(10) Patent No.: US 10,624,569 B2
(45) Date of Patent: Apr. 21, 2020

(54) METHOD OF INCREASING READING BARCODE INFORMATION

(71) Applicant: TYSON BIORESEARCH INC., Miaoli County (TW)

(72) Inventors: Andrew Yi Chen, Miaoli County (TW); Chih-Ching Chang, Miaoli County (TW); Jen-Hao Liu, Miaoli County (TW)

(73) Assignee: Tyson Bioresearch, Inc., Miaoli County (TW)

( * ) Notice: Subject to any disclaimer, the term of this patent is extended or adjusted under 35 U.S.C. 154(b) by 0 days.

(21) Appl. No.: 16/211,205

(22) Filed: Dec. 5, 2018

(65) Prior Publication Data

US 2019/0231242 A1   Aug. 1, 2019

Related U.S. Application Data

(60) Provisional application No. 62/624,810, filed on Feb. 1, 2018.

(51) Int. Cl.
| | |
|---|---|
| *A61B 5/15* | (2006.01) |
| *A61B 5/157* | (2006.01) |
| *A61B 90/96* | (2016.01) |
| *A61B 5/145* | (2006.01) |
| *A61B 5/1495* | (2006.01) |
| *G01N 33/487* | (2006.01) |

(52) U.S. Cl.
CPC ...... *A61B 5/150786* (2013.01); *A61B 5/1495* (2013.01); *A61B 5/14532* (2013.01); *A61B 5/157* (2013.01); *A61B 5/150022* (2013.01); *A61B 5/150358* (2013.01); *A61B 90/96* (2016.02); *G01N 33/48771* (2013.01); *A61B 2562/0295* (2013.01); *A61B 2562/08* (2013.01); *A61B 2562/226* (2013.01); *A61B 2562/227* (2013.01)

(58) Field of Classification Search
CPC ............ A61B 5/150786; A61B 90/96; A61B 5/14532; A61B 5/1495; A61B 5/150022; A61B 5/150358; A61B 5/157; G01N 33/48771
USPC .................................................. 235/462.01
See application file for complete search history.

(56) References Cited

U.S. PATENT DOCUMENTS

| | | |
|---|---|---|
| 2010/0041571 A1 | 2/2010 | Cohen |
| 2010/0119414 A1 | 5/2010 | Eisenhardt |

FOREIGN PATENT DOCUMENTS

| | | |
|---|---|---|
| CN | 206515242 U | 9/2017 |
| JP | S62-209684 A | 9/1987 |
| TW | M455473 U1 | 6/2013 |
| TW | M483498 U | 8/2014 |
| WO | 2015/134779 A1 | 9/2015 |

*Primary Examiner* — Daniel A Hess
(74) *Attorney, Agent, or Firm* — Winston Hsu (57) ABSTRACT

A blood glucose test strip includes a test strip, a blood test area formed on a first end of the test strip, an electrode formed on a second end of the test strip, a data barcode formed on the test strip, and a clock code formed on the test strip. The data barcode may include a plurality of first bars with spaces separating the first bars, each first bar having a width. The clock code may comprise a fixed pattern of second bars with spaces separating the second bars, a width of each second bar set according to the width of at least one of the first bars. The clock code can be used to calibrate the data barcode to compensate for insertion speed and/or moisture content.

11 Claims, 9 Drawing Sheets

Insert a test strip

Apple blood sample

Resuits in 5 seconds

An example of a label format

FIG. 11

METHOD OF INCREASING READING BARCODE INFORMATION

CROSS REFERENCE TO RELATED APPLICATIONS

This application claims the benefit of U.S. Provisional Patent Application No. 62/624,810, filed 2018 Feb. 1, and included herein by reference.

BACKGROUND OF THE INVENTION

1. Field of the Invention

This application relates to a blood glucose test strip, and more specifically to a blood glucose test strip utilizing a clock code to calibrate a data barcode.

2. Description of the Prior Art

The most efficient approach to take care of one who is diabetic is to monitor his blood glucose level constantly. By adjusting food intake, exercise, and medicine, a thorough diabetic care plan can be established to control the blood glucose level and reduce the chances of getting other complications.

Figure 1:
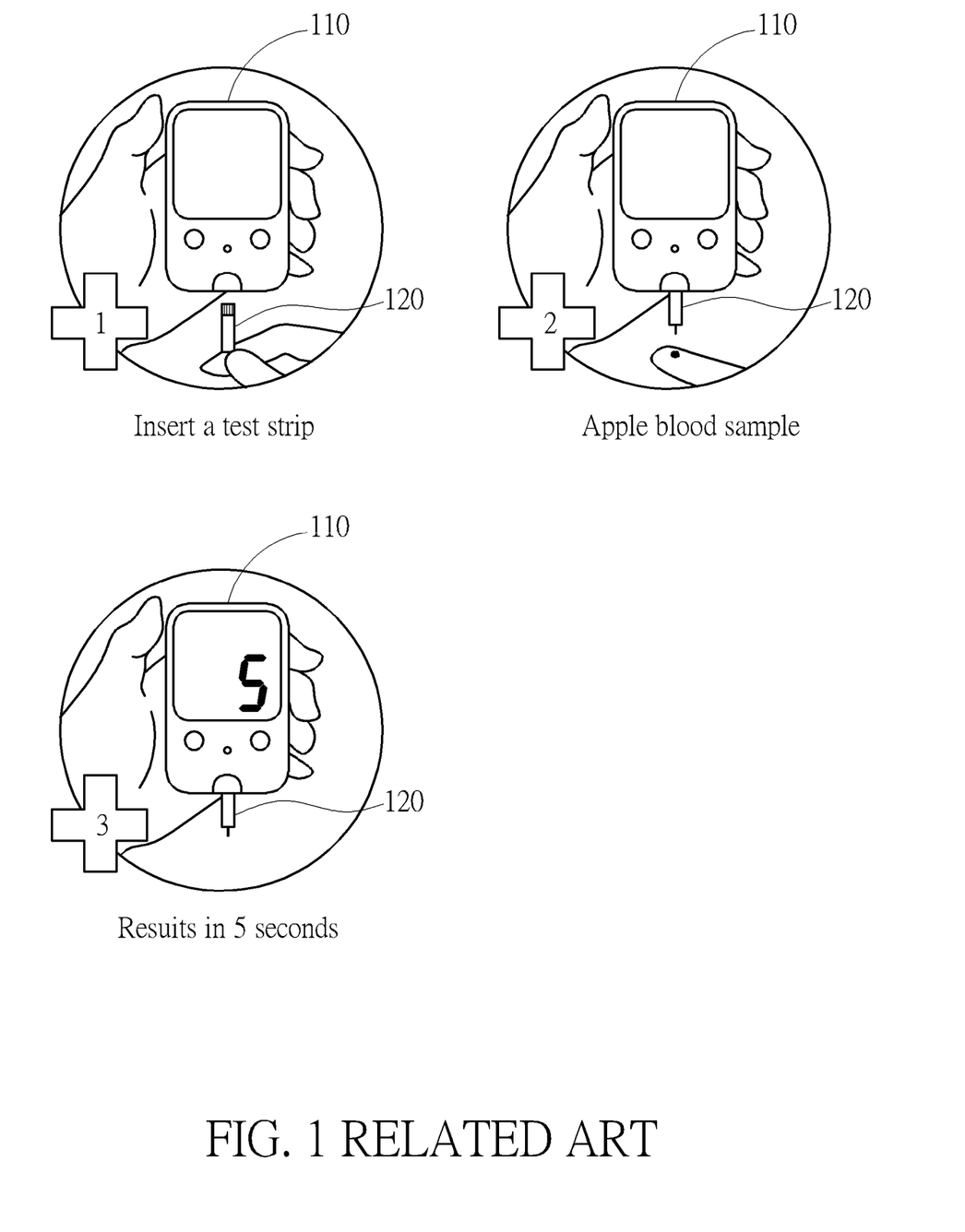
FIG. 1 illustrates a conventional blood glucose monitoring system.
Figure 2:
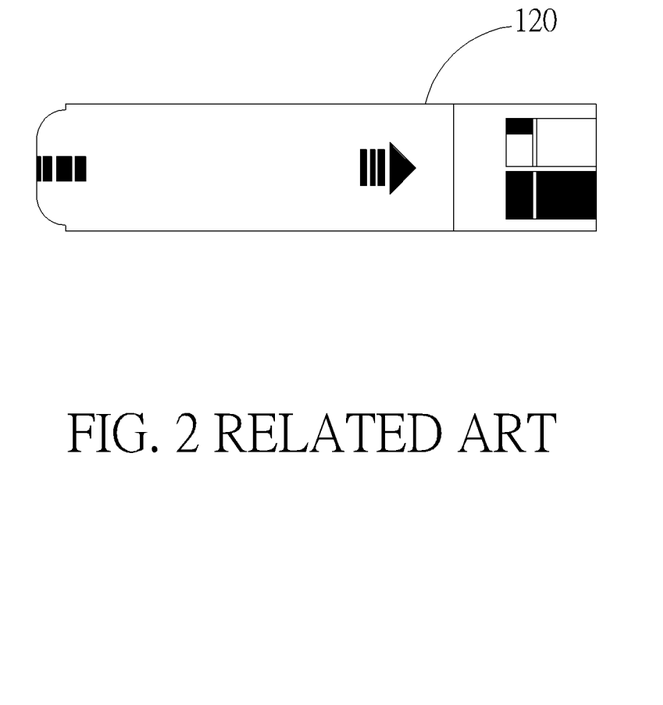
FIG. 2 illustrates a conventional blood glucose test strip.

A blood glucose monitoring system 100 (as shown in FIG. 1: Tyson blood glucose monitoring system) comprises a blood glucose meter and a blood glucose test strip 120 (also shown in FIG. 2). When blood glucose is to be tested, remove a blood glucose test strip 120 from a blood glucose test strip storage jar (not shown), insert the test strip 120 into the blood glucose meter 110, extract blood from a finger, then wait for the blood glucose meter 110 to analyze blood glucose.

SUMMARY OF THE INVENTION

A blood glucose test strip may comprise a test strip, a blood test area formed on a first end of the test strip, an electrode formed on a second end of the test strip, a data barcode formed on the test strip, and a clock code formed on the test strip. The data barcode may comprise a plurality of first bars with spaces separating the first bars, each first bar having a width. The clock code may comprise a fixed pattern of second bars with spaces separating the second bars, a width of each second bar set according to the width of at least one of the first bars. The clock code can be used to calibrate the data barcode to compensate for insertion speed and/or moisture content.

A method of utilizing a blood glucose test strip comprises providing a test strip, the test strip comprising a blood test area formed on a first end of the test strip, an electrode formed on a second end of the test strip, a data barcode formed on the test strip, and a clock code formed on the test strip. The test strip is inserted into a meter, the meter comprising a barcode scanner generating a first electrical signal according to the data barcode and a second electrical signal according to the clock code during insertion of the test strip. The second electrical signal is utilized to calibrate the first electrical signal to retrieve correct data barcode data, compensating for insertion speed and/or moisture content.

These and other objectives of the present invention will no doubt become obvious to those of ordinary skill in the art after reading the following detailed description of the preferred embodiment that is illustrated in the various figures and drawings.

DETAILED DESCRIPTION

There are many types of blood glucose test strips for sale in the market. To avoid consumers misusing other brands or inferior counterfeit blood glucose test strips, some blood glucose test strips have themselves identified in a blood glucose meter 110 to prevent a blood glucose meter user from using an inferior counterfeit blood glucose test strip to test blood glucose.

If an inferior blood glucose test strip causes the blood glucose meter to err, causing false reading of the blood glucose level and a delay in treating a patient, this may lead the patient to a critical condition.

Thus, Taiwan Patent Application published as TW201329451 has disclosed a structure that can automatically identify the model number of a blood glucose test strip, particularly a structure that can use an attached code to automatically identify the model number of a blood glucose test strip. The technical scope discloses connecting conductive components such as a conductive strip, electrode, reaction layer, test node, verification node and lead wire for identifying the blood glucose test strip. The identifiable information of the test strip may also include a production batch number, variations in production, test strip type, etc. Any mechanism and function of the inserted test strip identifiable by the blood glucose meter belong to the test strip identification system. However, the length, width and height of this type of test strip are less than 50 mm, 10 mm and 2 mm respectively. It is very difficult to create a plurality of sets of identification data in such a small space and enable the blood glucose meter to access the data, thus RFID chips are disposed on some of the test strips to enable the blood glucose meter to identify the test strips. However, since test strips are consumables, it may not be cost effective to dispose an additional chip.

Imprinting a set of barcode tags on the surface of the blood glucose test strip to form a test strip identification system is a more cost effective way. Barcode scanning is a linear scan performed by an optical pickup and an optical sensor called a charge-coupled element (CMOS or CCD). The optical pickup can be disposed in the blood glucose meter for reading the barcode. However, the size and internal space of a hand held blood glucose meter have a limit because the blood glucose meter does not have enough space for performing a complete linear barcode scan after the blood glucose test strip is inserted.

Figure 3:
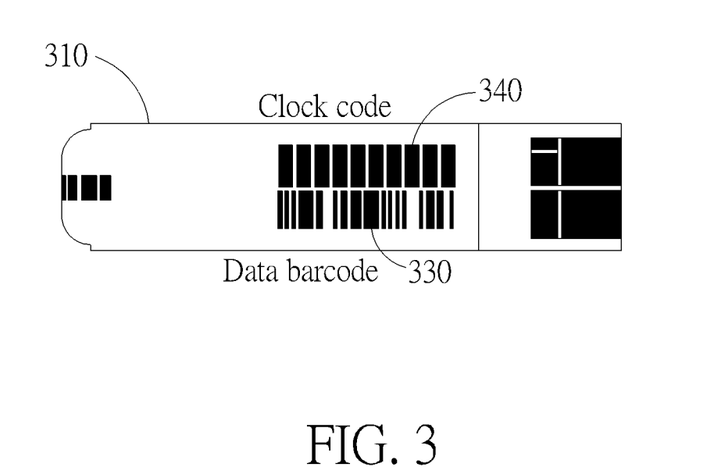
FIG. 3 illustrates a set of two one-dimensional barcodes according to an embodiment.
Figure 4:
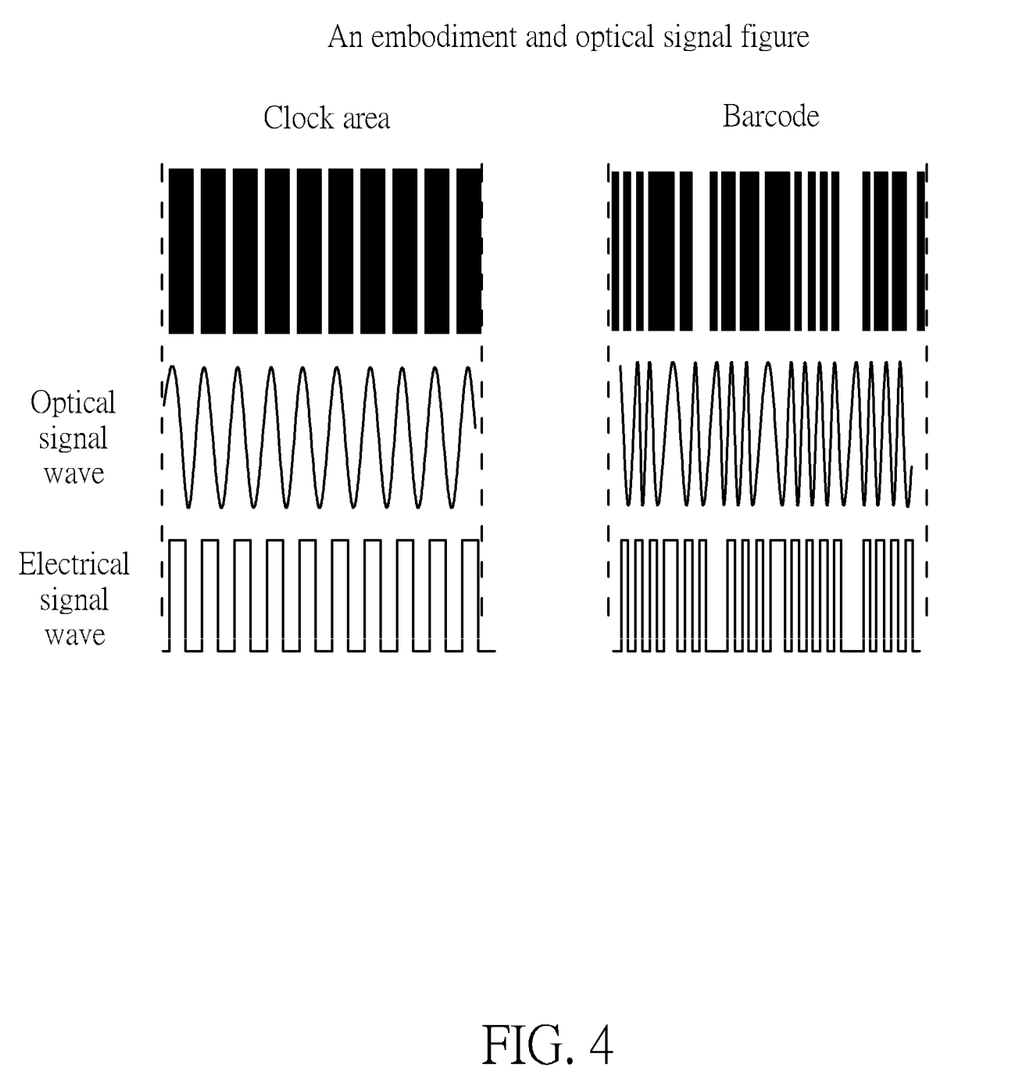
FIG. 4 illustrates an example conversion by an optical reader, through reading reflectance (R %), optical analog signals into digital signals.

One of the feasible approaches is to scan with a single dot optical reader. The linear scan is performed during the insertion of the test strip. The set of barcode tags comprise two one-dimensional barcodes, namely a data barcode 330 and a clock code 340 (as shown in FIG. 3). The barcode tags can be identified during the insertion of the blood glucose test strip 310 into the blood glucose meter. The dimension of the data barcode 330 is determined by the smallest readable area of the optical reader. The data barcode 330 is generated according to the real code, lot number, expiration date, strip vial ID, etc. of the product. The dimension of the data barcode 330 is determined by the least analyzable scope of the optical reader. After the data barcode 330 is accessed by the optical reader through reading reflectance (R %), optical analog signals are generally converted into digital signals for storage (as shown in FIG. 4).

A common barcode resolution will affect the dimension of the tag. A higher resolution allows a smaller width, reducing the size of the tag. However, the higher resolution has its limit, often the highest resolution is determined by the specification of the optical reader for accessing the barcode (often annotated as 0.127 mm or 5 mils, and the thinnest bar cannot be thinner than the annotated value) (reference data source: http://wss-barcode.blogspot.tw/2008/05/blog-post_195.html). Alternatively, barcodes with different width can be designed according to high, medium and low resolutions of the optical reader. (High resolution: Width<0.23 mm, Medium resolution: Width=0.23-0.5 mm, Low resolution: Width>0.5 mm) (reference data source: http://www.unitesys.com.tw/unitesys/main/km.asp).

When the test strip 310 only has a 1D data barcode 330 thereon, the meter can access basic information of the product. If a clock code 340 is added, then when inserting the test strip 310, the reading error of the optical reader caused by an inconsistent insertion speed of the test strip 310 can be reduced.

Figure 5:
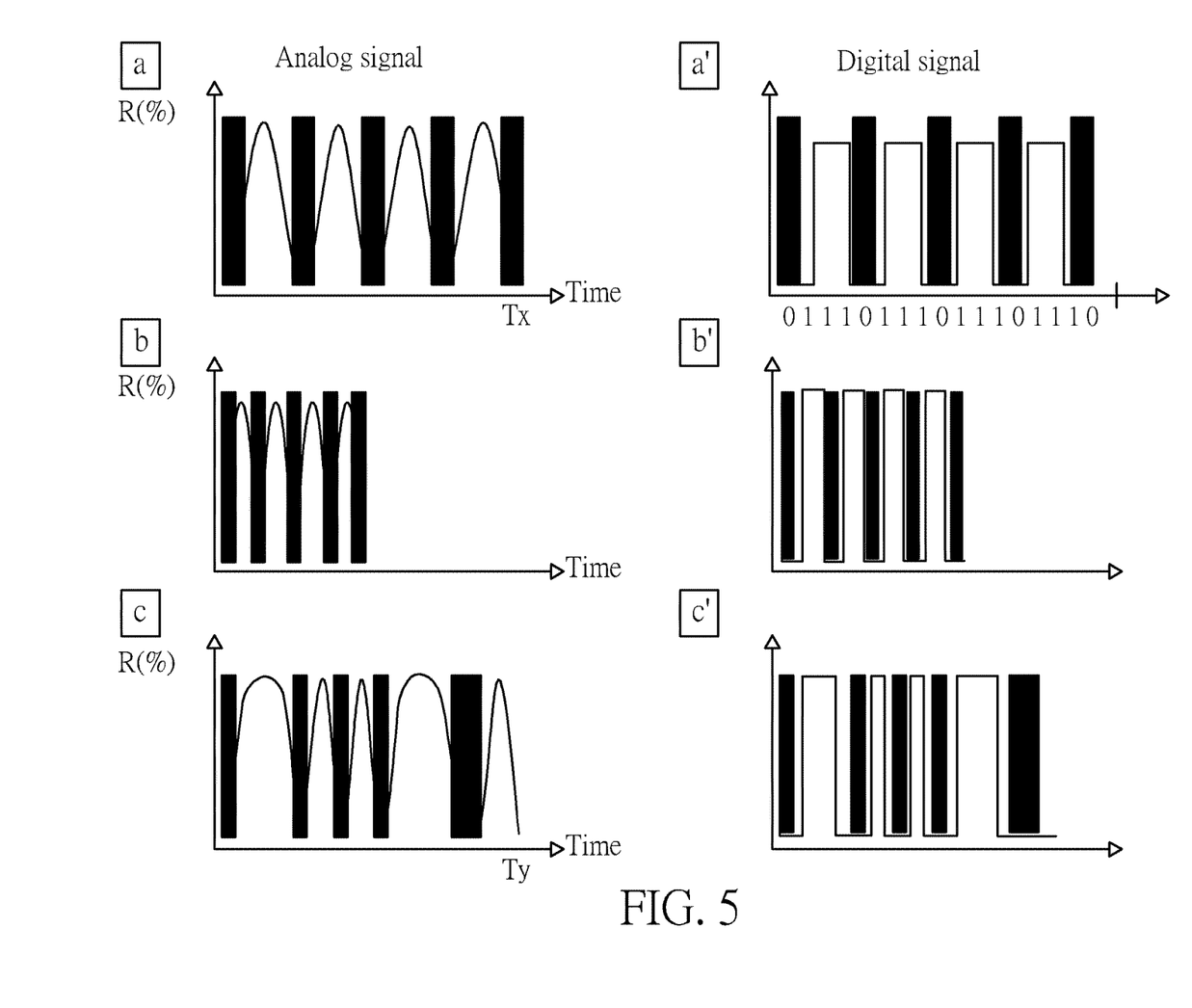
FIG. 5 is a brief diagram showing an optical analog signal and digital signal when the test strip is inserted at an inconsistent speed.

FIG. 5 is a brief diagram showing an optical analog signal [FIG.a-FIG.c] and digital signal [FIG.a'-FIG.c'] when the test strip 310 is inserted at an inconsistent speed. As shown by the scanned clock code in FIG. 5, FIG.a shows a valid identifiable optical figure (assuming there are 5 bars, barcode scan time is Tx, scan speed is Va). FIG.b shows the test strip insertion speed is twice of FIG.a, reducing the scan time to (½)Tx. If the test strip 310 is inserted at an unstable speed, the scanned barcode may become FIG.c, showing equal distant bars unevenly distributed. Since different widths of bars and spacings represent different values, FIG.c shows that an error has occurred during the scan process. To avoid the error caused by the inconsistent insertion speed of the test strip, a preset scan signal value can be established first in the strip scanner. When the scan speed is inconsistent, the error signal can be fed back to the scanner for calibration, followed by identifying the barcode to obtain a more correct data barcode.

The 2D barcode can access more codes in a limited space, however its optical reader should be more sophisticated than that of 1D barcode. The 2D barcode reader must have a linear or planar optical sensor, such a sensor if only used to access the barcode of the test strip would tremendously increase the cost of blood glucose meter, making it less cost effective. Thus using a dot sensor for reading the 1D barcode is more economical. The number of values encoded in the 1D barcode can be adjusted by lengthening or shortening the barcode. If more values are to be encoded, and the resolution of the optical reader remains unchanged, the barcode should be lengthier. However, the length of the test strip is only 50 mm. After deducting the blood insertion terminal and signal terminal, the test strip can only accommodate a test strip of 30 mm. Thus, space is limited. Since there is a required number of values to be encoded, only the width can be manipulated to increase the number of encoded values. In addition to encode at least one data barcode, a clock code should be added to calibrate the error caused by the inconsistent insertion speed of the test strip.

Figure 6:
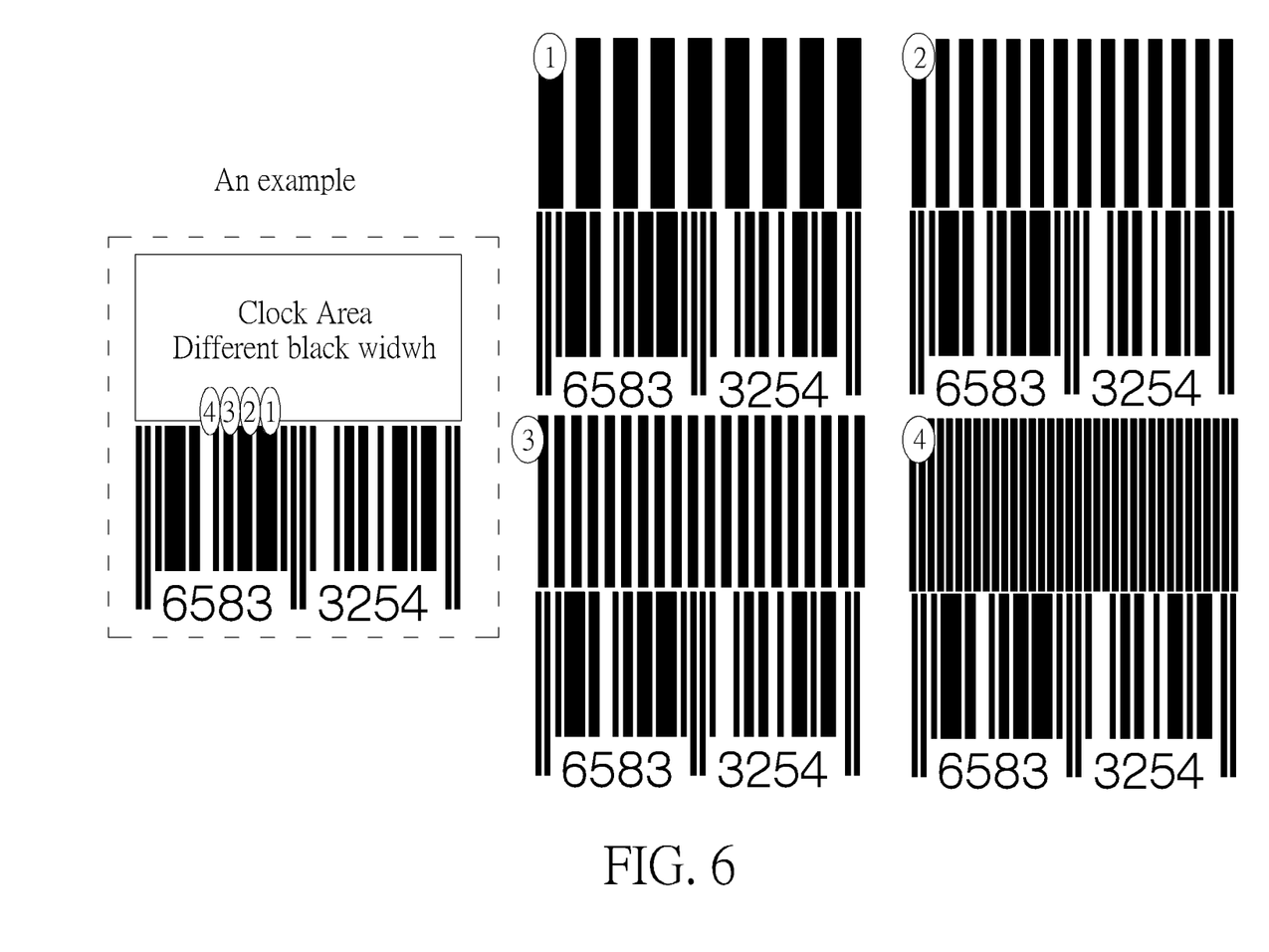
FIG. 6 illustrates how 4 clock codes can each have the same width as a corresponding one of the 4 different widths of the data barcode.

The design of the clock code 340 can be based on the data barcode 330. For instance, if the data barcode 330 is encoded with 4 different widths, 4 clock codes 340 of 4 different widths can be used to match with the data barcode. The 4 clock codes 340 can each have the same width as a corresponding one of the 4 different widths (as shown in FIG. 6). Thus, 4 times of encoded data can be retrieved. Each test strip can have a clock code 340, which matches the width of its data barcode. This will allow more encoded data to be retrieved from each test strip 310.

Figure 7:
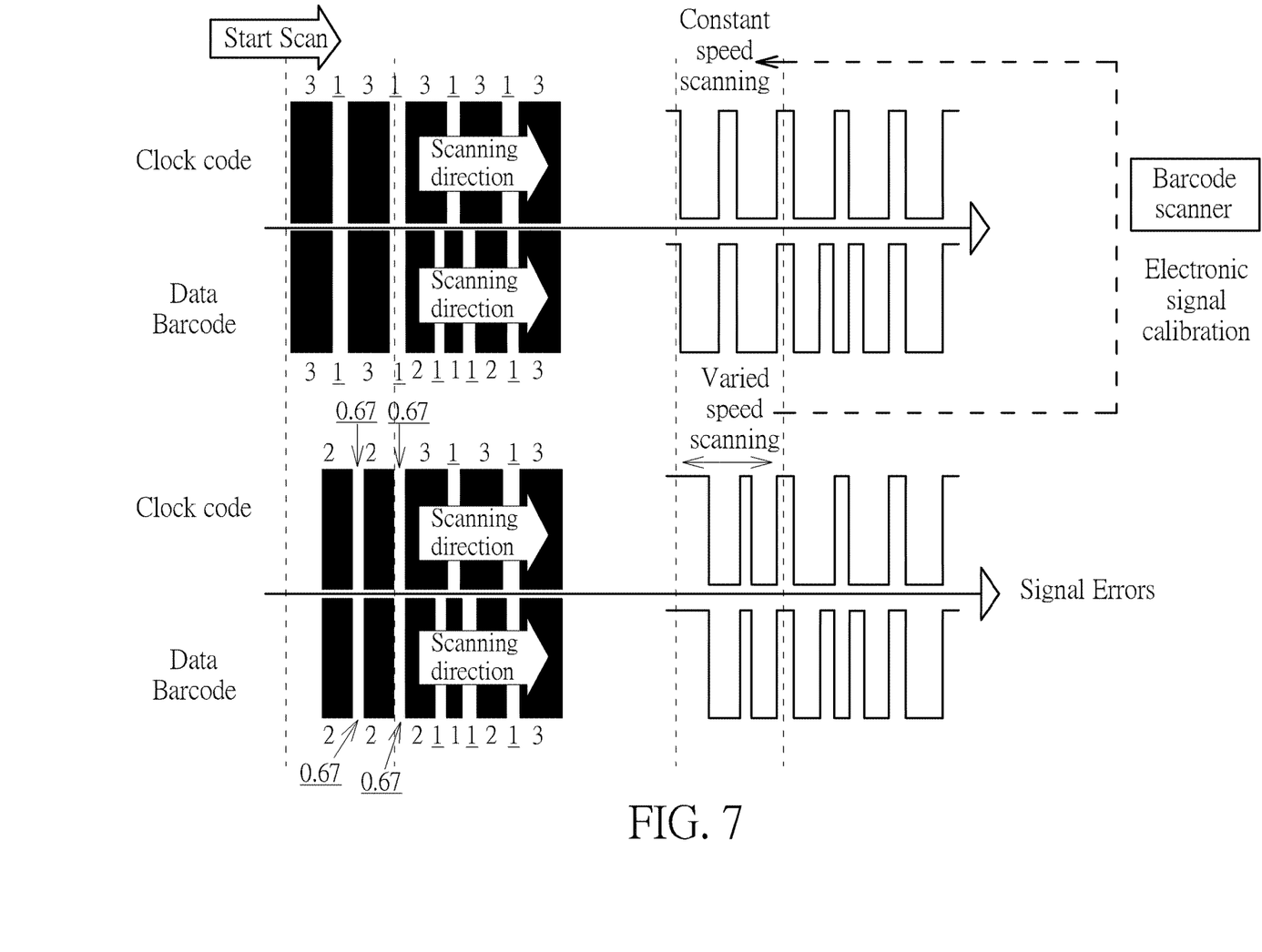
FIG. 7 shows results from an embodiment of the present invention when the test strip is scanned at a fixed speed and when the test strip is inserted at a higher speed initially.

FIG. 7 shows an embodiment of the present invention. The bars of data barcode 330 have three different widths. The least bar width is named "unit width 1", and the other two widths are named "unit width 2" and "unit width 3" respectively. Thus, the data barcode in the embodiment is called "332123", and the spacings have a width equal to the least bar width "unit width 1". The upper left diagram of FIG. 7 has a clock code 340. The width of the bars of the clock code 340 is assumed to be "unit width 3", the width of its spacings is "unit width 1". When scanning the barcode 330, suppose the clock code at the upper left diagram of FIG. 7 is scanned at a fixed speed Vx, then a digital signal as the upper right diagram of FIG. 7 would be generated. The optical waveform is a clock waveform with the same period and pulse width.

The lower diagram of FIG. 7 shows that the test strip is inserted at a higher speed initially, thus the scanned number "33" is erred, "unit width 3" becomes "unit width 2". When generating the digital signal, a signal error would be generated as shown in the lower right diagram. The signals in the barcode scanner can be used to calibrate the clock code 340, then the data barcode 330 can be calibrated at the same time thereby retrieving the correct data barcode 330 and serving the purpose of the clock code 340.

Figure 8:
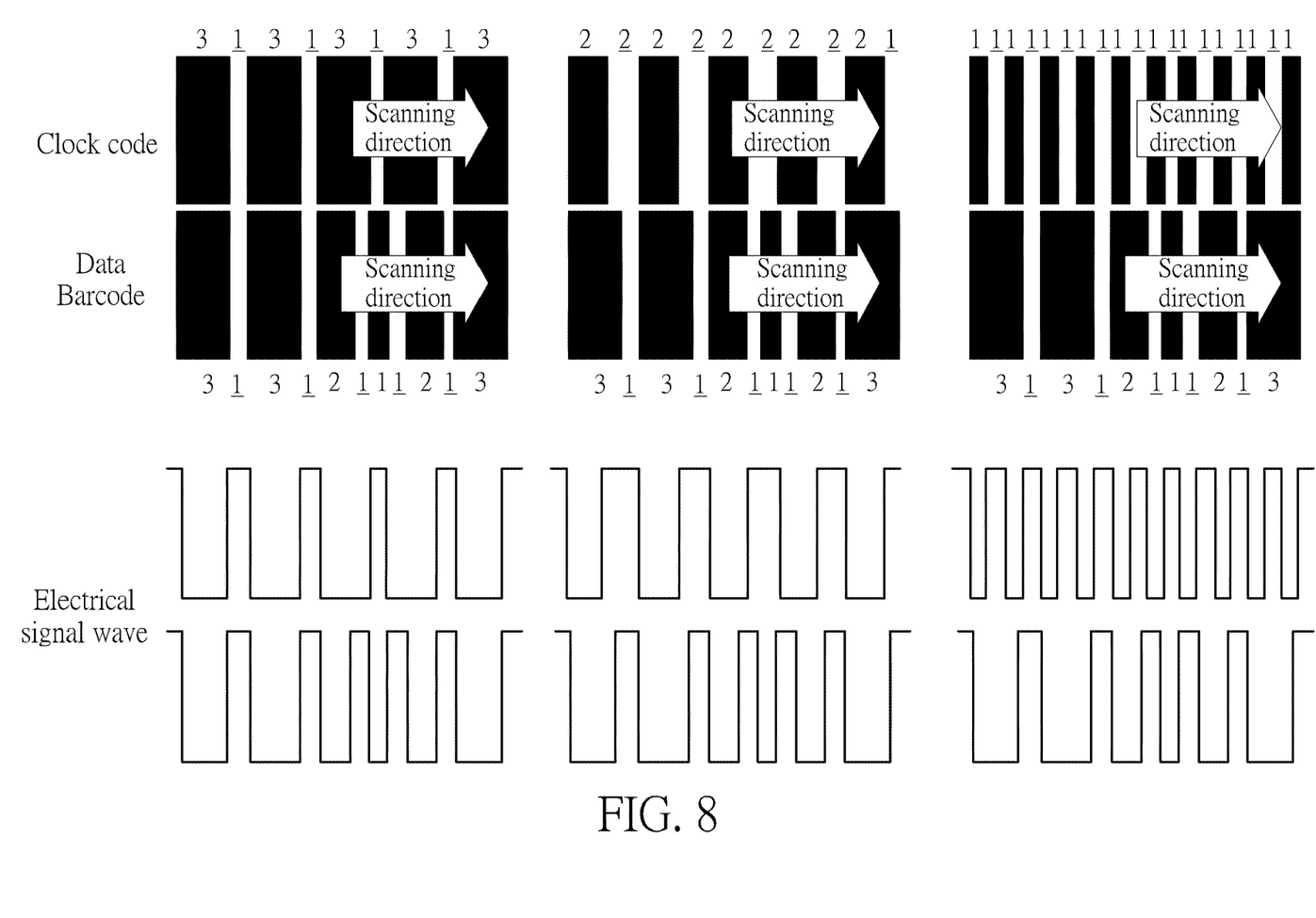
FIG. 8 illustrates three embodiments of clock codes.

Please refer to three embodiments of clock codes in FIG. 8. The upper portion refers to clock codes, the lower portion refers to the data barcode, and the two are aligned. When at least two dot optical sensors are scanning the two codes separately at the same time, the data barcode would be six digits and determined by the widths of the bars to be "332123". The spacings are equally distant. The bar width of the clock code can be set according to bar widths of the data barcode, the widths of the bars of the clock code are the same, and the spacings of the clock code are also the same. When inserting the test strip to the blood glucose meter, the optical signals received by the optical sensor are sequentially converted to analog signals as shown in the lower half of the figure. The amount of data of the data barcode is known, the amount of data of the clock code is also known. For instance, the clock code with "unit width 3" has five bars, the clock code with "unit width 1" has ten bars, by referencing each other more data can be retrieved. In this embodiment, three encoded values "332123-3", "332123-2" and "332123-1" are retrieved. Comparing to the data barcode with one clock code, which can only retrieve "332123", triple amount of data is retrieved from the data barcode.

The present invention is not limited to the aforementioned embodiment. For example, the bar width of the clock code can be different from the bar widths and spacings of the data barcode. The bar width and spacings of the clock code can be different. Any clock code having a fixed pattern used to calibrate a data barcode with an inconsistent scanning speed can be called a clock code.

Figure 9:
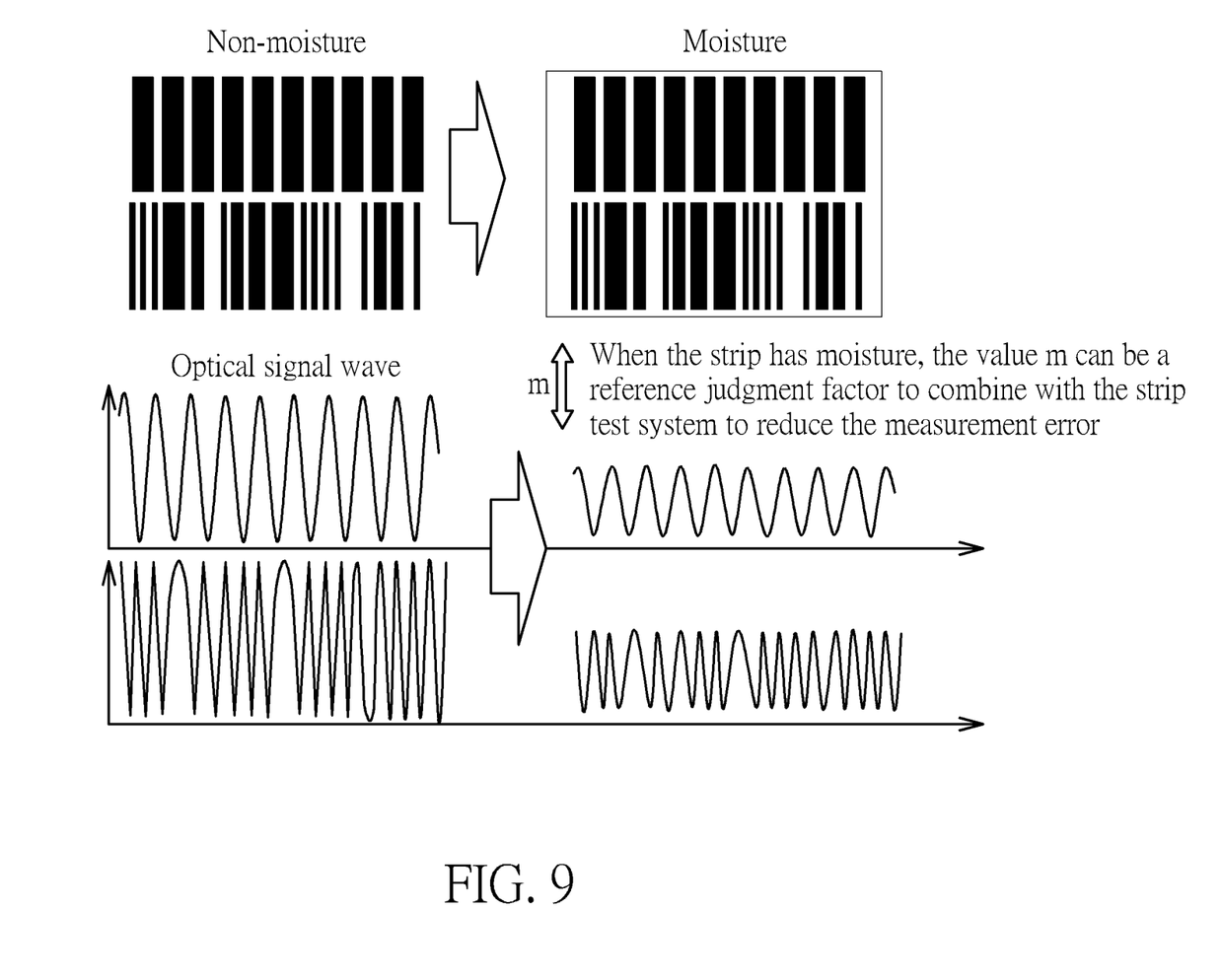
FIG. 9 illustrates the effects of a dampened test strip.

Most commercial blood glucose test strips face a damping issue after a storage jar is opened. Thus, many commercial products come with a damp-proof design, such as adding a damp-proof device in the storage jar (e.g. TW M482562) or imposing damp-proof measures on the package of the test strip (e.g. TW M399102), etc. However, none is able to calibrate the final measurement according to errors caused by damping. In an embodiment of the present invention, when scanning the data barcode, damping information can be retrieved at the same time, by identifying the relationship between damping information and measurement, errors can be calibrated, making measurement more accurate. When the barcode optical reader scans the barcode, the reflectance of undampened spacings in the optical graph generated thereby can be set to be 100. After the test strip is dampened, the reflectance decreases, the dampened waveform will be clearly different from the undampened waveform (as shown in FIG. 9). Then the difference of reflectance R (%) can be used as a basis for calibrating the damped test strip. In an embodiment of the present invention, the undampened test strip should have a white body. After it is dampened, the white body will turn to slightly pinkish. In the optical reader, perceiving from the angle of the optical meter, the reflectance has decreased. The relationship between changes in the reflectance and the extent of dampening of the test strip can be established by experiment. This test strip measurement can be calibrated by the extent the analog signal generated by the optical reader has decreased. In another design, the measurement of the first test strip taken out from the storage jar after it is opened can be saved in the blood glucose meter as a basis. As time goes by, other test strip will be dampened, and their measurements can be calibrated according to the measurement of the first test strip.

The present invention discloses a blood glucose test strip that has a data barcode and has a mechanism for calibrating its dampening effect. While inserting the test strip into the blood glucose meter, the data barcode is scanned, and the test error caused by the dampening effect of the test strip is calibrated by the calibration mechanism. The present invention uses the two advantages to enhance the test accuracy of the blood glucose test strip.

Figure 10:
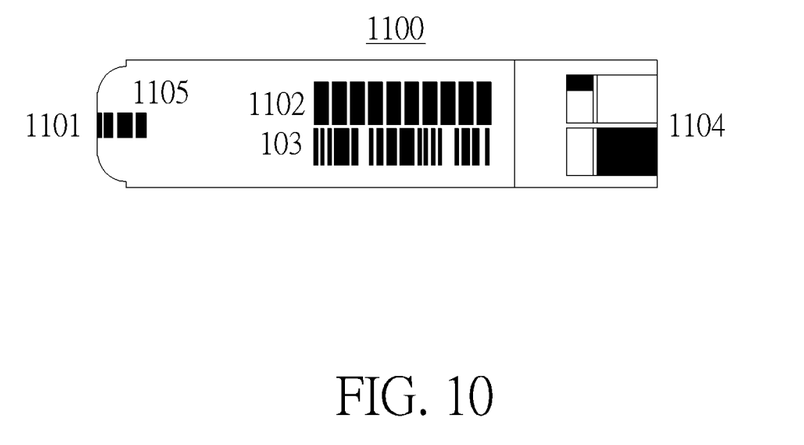
FIG. 10 is an embodiment of a blood glucose test strip of the present invention.

FIG. 10 is an embodiment of a blood glucose test strip 1100 of the present invention. The blood glucose test strip 1100 comprises a test strip 1105, a blood test area 1101, a test strip electrode 1104 for providing electrical connection with a meter, a clock code 1102, and a data barcode 1103.

Figure 11:
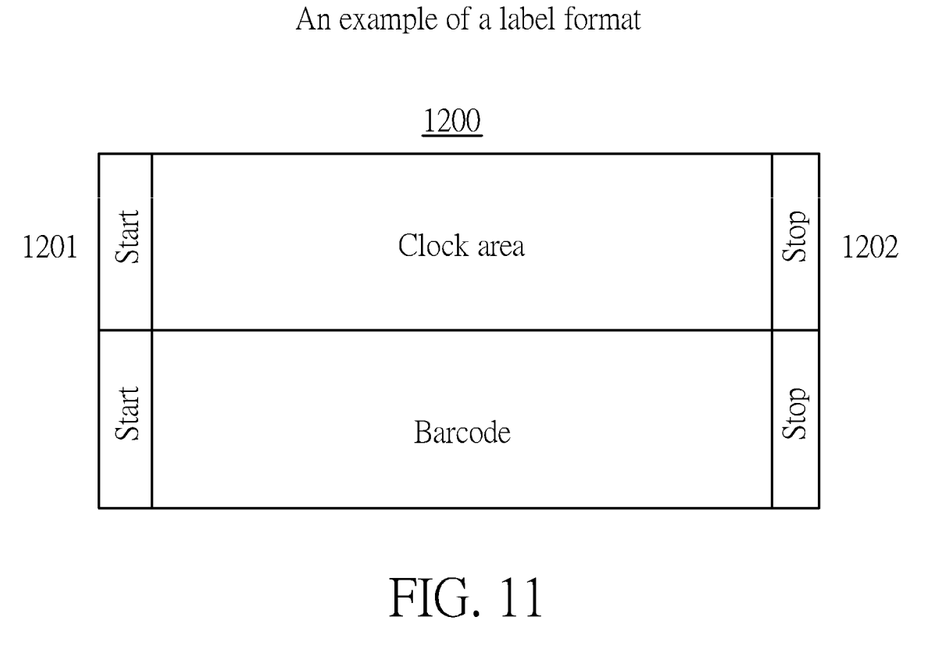
FIG. 11 is a brief diagram of the clock code and the data barcode of the present invention.

FIG. 11 is a brief diagram of the clock code and the data barcode of the present invention. When starting to identify the barcode, the barcode comprises a "START" region 1201. The region comprises a plurality of bars to inform the scanner that scanning of the data barcode is about to begin. At the end of scanning process, the barcode comprises a "STOP" region 1202. The region comprises a plurality of bars to inform the scanner that scanning of the data barcode is about to end. The design of "START" and "STOP" has been widely used in the prior art. They can also be used in the clock code to indicate start of end of the scanning process, not to be used to calibrate the data barcode. Thus the start and end portions may not have an equal distant arrangement. They are not included in the design of the barcode of the present invention.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. A blood glucose test strip comprising:
    a test strip;
    a blood test area formed on a first end of the test strip;
    an electrode formed on a second end of the test strip;
    a data barcode formed on the test strip, the data barcode comprising a plurality of first bars with spaces separating the first bars, at least one of the first bars having a first width and at least one of the first bars having a second width that is different than the first width; and
    a clock code formed on the test strip, the clock code comprising a fixed pattern of second bars with spaces separating the second bars, a width of each second bar equal to the first width.

2. The blood glucose test strip of claim 1, wherein all second bars have a same width.

3. The blood glucose test strip of claim 1, wherein the data barcode includes information according to at least one of a real code, lot number, expiration date, and strip vial ID of the test strip.

4. Method of utilizing a blood glucose test strip comprising:
    providing a test strip, the test strip comprising:
        a blood test area formed on a first end of the test strip;
        an electrode formed on a second end of the test strip;
        a data barcode formed on the test strip, the data barcode comprising a plurality of first bars with spaces separating the first bars, at least one of the first bars having a first width and at least one of the first bars having a second width that is different than the first width; and
        a clock code formed on the test strip, the clock code comprising a fixed pattern of second bars with spaces separating the second bars, a width of each second bar equal to the first width;
    inserting the test strip into a meter, the meter comprising a barcode scanner generating a first electrical signal according to the data barcode and a second electrical signal according to the clock code during insertion of the test strip;
    utilizing the second electrical signal to calibrate the first electrical signal to retrieve correct data barcode data.

5. The method of claim 4, further comprising forming all second bars to have a same width.

6. The method of claim 4, further comprising forming the data barcode to include information according to at least one of a real code, lot number, expiration date, and strip vial ID of the test strip.

7. The method of claim 4, further comprising referencing the clock code to retrieve more data than is retrieved from the data barcode.

8. The method of claim 4, further comprising measuring reflectance of the test strip while the test strip is inserted into the meter.

9. The method of claim 8, further comprising calibrating test strip measurements according to the measured reflectance.

10. The method of claim 9, further comprising calibrating test strip measurements according to the extent analog signal generated by an optical reader of the meter has decreased from a predetermined value.

11. The method of claim 4, further comprising utilizing the clock code to calibrate the data barcode to compensate for insertion speed of the test strip into the meter.

* * * * *